United States Patent [19]

Merten et al.

[11] 4,323,687

[45] Apr. 6, 1982

[54] PROCESS FOR THE PREPARATION OF 1,2,4-TRIAZOLIDINE-3,5-DIONE

[75] Inventors: Rudolf Merten, Leverkusen; Ludwig Rottmaier, Odenthal, both of Fed. Rep. of Germany

[73] Assignee: Bayer Aktiengesellschaft, Leverkusen, Fed. Rep. of Germany

[21] Appl. No.: 208,870

[22] Filed: Nov. 21, 1980

[30] Foreign Application Priority Data

Nov. 26, 1979 [DE] Fed. Rep. of Germany ....... 2947619

[51] Int. Cl.$^3$ ............................................. C07D 249/12
[52] U.S. Cl. ................................................... 548/264
[58] Field of Search ......................................... 548/264

[56] References Cited

FOREIGN PATENT DOCUMENTS 772625 11/1967 Canada ................................. 548/264

OTHER PUBLICATIONS

Thiele et al., Liebigs Annalen der Chemie, vol. 283, p. 41, (1894).
Pellizzari et al., Gazz. Chim. Ital., vol. 24, p. 506, (1894).

*Primary Examiner*—Alton D. Rollins
*Attorney, Agent, or Firm*—Connolly and Hutz

[57] ABSTRACT

A process for the preparation of 1,2,4-triazolidine-3,5-dione, which comprises suspending hydrazodicarbonamide in at least one organic, optionally water-miscible solvent and cyclising it at a temperature in the range of from 150° to 280° C. and at a pressure of from 50 mbar to 5 bar with removal of the ammonia split off from the reaction mixture, and isolating the resulting 1,2,4-triazolidine-3,5-dione after crystallization.

7 Claims, No Drawings

PROCESS FOR THE PREPARATION OF 1,2,4-TRIAZOLIDINE-3,5-DIONE

This invention relates to a process for the preparation of 1,2,4-triazolidine-3,5-dione by heating hydrazo-dicarbonamide in a least one organic solvent.

The preparation of 1,2,4-triazolidine-3,5-dione from hydrazodicarbonamide is known. It is carried out (as described in Liebigs Annalen der Chemie Vol. 283, page 41 (1894) by solvent-free heating of hydrazodicarbonamide, but this method can hardly be carried out on a technical scale. The molten product obtained is heavily contaminated and solidifies on cooling to a hard mass which must be broken down for further processing and purified. The yields of 1,2,4-triazolidine-3,5-dione are in the region of 40% to 50% of the theoretical yield.

It is an object of the present invention to provide a process for the preparation of 1,2,4-triazolidine-3,5-dione from hydrazodicarbonamide which is technically easy to carry out and by which 1,2,4-triazolidine-3,5-dione can be obtained in a crystalline form, in a high yield and with a high degree of purity.

The problem was solved by cyclising hydrazodicarbonamide in organic solvents (organic reaction media) under special operating conditions.

The present invention thus provides a process for the preparation of 1,2,4-triazolidine-3,5-dione from hydrazodicarbonamide by cyclisation at elevated temperatures with elimination of ammonia, characterised in that hydrazodicarbonamide is suspended in at least one organic solvent, optionally one which is miscible with water, and is cyclised at temperatures of from 150° C. to 280° C. at a pressure of from 50 mbar to 5 bar while ammonia split off in the reaction is removed from the reaction mixture, and the resulting 1,2,4-triazolidine-3,5-dione is isolated after crystallisation.

The process according to the invention results in uniformly high yields of 1,2,4-triazolidine-3,5-dione without the formation of (polymeric) by-products. The solvent medium may be repeatedly used in numerous reaction cycles, in most cases without purification. Another, specific advantage is that moist, crude starting material may be used without a drying process.

The organic solvents used in the process according to the invention should have sufficient thermal stability under the reaction conditions and be chemically inert towards hydrazodicarbonamide and triazolidine-3,5-dione and they should have a sufficiently high boiling point so that they will not distil over during the reaction. The boiling points of the solvents are generally at least 150° C. at atmospheric pressure, preferably about 200° C. to 250° C. The solvents may be miscible, partly miscible or immiscible with water at room temperature.

Hydrazodicarbonamide is virtually insoluble in the solvents, and its cyclisation product, 1,2,4-triazolidine-3,5-dione, in some cases also has only limited solubility in the solvents. The reaction mixture may thus be in the form of an emulsion after cyclisation and before crystallisation, and the solvent may be regarded as the reaction medium.

The following solvents are suitable:

(A) Nitrogen-containing solvents substituted with phenyl or $C_1$–$C_6$ alkyl groups on the nitrogen atom, e.g. N-substituted pyrrolidones, urethanes, cyclic urethanes or ureas such as N-methylpyrrolidone, ethyl-phenylurethane, 5-methyl-2-oxazolidinone or tetra-methylurea; polyethers, e.g. diethylene glycol diethlether; phenols such as cresols, halogen-substituted phenols and cresols, e.g. 4-chlorophenol: dialkylsulphones and cylic sulphones each with a maximum of 12 carbon atoms, e.g. dimethylsulphone or sulpholane; aromatic or araliphatic ethers such as diphenylether and dibenzylether.

(B) Further suitable solvents are: Aliphatic, cycloaliphatic, aromatic and araliphatic hydrocarbons and commercial mixtures thereof, e.g. dodecane, decalin, trimethylbenzene, naphthalene, 1-methyl-naphthalene, diphenylmethane, halogenated aliphatic, cycloaliphatic, aromatic and araliphatic hydrocarbons such as dodecyl chloride, 1,2,4-trichlorobenzene, 1-chloronaphthalene and dichlorotoluene, and commercial mixtures of such hydrocarbons.

Diphenylether, diphenylmethane, 1-methylnaphthalene, dialkylsulphones and cyclic sulphones are particularly preferred, especially sulpholane.

The reaction mixtures obtained after cyclisation in the polar solvents such as those listed under (A) above may be mixed during the cooling process with solvents which are inert towards 1,2,4-triazolidine-3,5-dione, such as aliphatic, cycloaliphatic, araliphatic or aromatic hydrocarbons, e.g. cyclohexane, toluene and xylene and aliphatic or cycloaliphatic alcohols, e.g. butanol or cyclohexanol and ethers or esters derived from them, e.g. glycol monomethylether or butyl acetate, and ketones such as acetone or ethyl methyl ketone, or also water if the polar solvents used are water-miscible, the addition of these inert solvents enabling 1,2,4-triazolidine-3,5-dione to crystallise from the reaction mixture in higher yields and with a higher degree of purity. The quantity of these added solvents may be up to 500% by weight, based on the polar solvent.

The hydrazodicarbonamide to be used in the process according to the invention is known from the literature and is obtained in virtually quantitative yield by the reaction of 1 mol of hydrazine with 2 mols of urea in an aqueous medium with elimination of ammonia. The hydrazodicarbonamide precipitating in the reaction is isolated by suction filtration and is immediately ready for use as a wet filter cake if the residual water can be removed in the process of cyclisation. Dehydrated or dried hydrazodicarbonamide may, of course, also be used for subsequent reactions, or the suspension of hydrazodicarbonamide obtained in water may be heated to distil off the water after the addition of a suitable solvent according to the invention, and the hydrazodicarbonamide left behind may be cyclised to 1,2,4-triazolidine-3,5-dione.

For cyclisation, the hydrazodicarbonamide is suspended in at least one of the organic solvents mentioned. The initial concentrations are preferably from 10 to 70% by weight, i.e. 100 g of reaction mixture contain from 10 to 70 g of hydrazodicarbonamide. Initial hydrazodicarbonamide concentrations of from 10 to 50% by weight are particularly preferred.

The reaction temperature employed in the process according to the invention is from 150° to 280° C., preferably from 170° to 250° C. and most preferably from 190° to 220° C. The higher the temperature, the faster is the reaction, although the risks of formation of unwanted by-products and decomposition of the solvent also increase.

The reaction times generally range from 0.5 to 10 hours but may lie above or below these limits in exceptional cases.

The reaction pressure employed in the process according to the invention is from 50 mbar to 5 bar. If the pressure rises above atmospheric pressure, the ammonia released in the reaction must be discharged from time to time to enable cyclisation to be carried out within the preferred pressure range of 150 mbar to atmospheric pressure.

It is advantageous in the process according to the invention if the concentration of ammonia split off is kept low in the reaction vessel. This may be achieved by known methods, e.g. by blowing out with an inert gas such as air, nitrogen, carbon dioxide or steam. The ammonia may also be driven off with low boiling solvents such as aliphatic, aromatic or araliphatic hydrocarbons or commercial mixtures thereof or chlorinated hydrocarbons having preferably 1 to 10 carbon atoms, such as cyclohexane, toluene, xylene, petroleum ether or chloroform by pumping them as liquids into the reactor or introducing them dropwise. Alternatively, the partial pressure of ammonia may be reduced by suction if the reaction is carried out at sub-atmospheric pressure.

The process according to the invention is suitable both for batchwise and for continuous operation. In a continuous operation, cyclisation is carried out by known methods, e.g. using cascades or tube reactors. The batchwise process is preferred.

If the process is carried out in water-miscible polar solvents, the 1,2,4-triazolidine-3,5-dione is in most cases worked up by leaving it to crystallise from the hot triazolidine-3,5 dione solution on cooling and isolating it by suction filtration, whereby it is obtained in a virtually pure form. This commercial 1,2,4-triazolidine-3,5-dione can generally be used immediately but if an exceptionally pure product is required it may be recrystallised, e.g. from water.

One particularly preferred embodiment consists of the preparation of 1,2,4-triazolidine-3,5-dione from hydrazodicarbonamide in sulpholane at temperatures of from 200° to 210° C. and a pressure in the reactor of from 200 to 550 mbar produced by a water jet vacuum. The ammonia released is removed for further use while 1,2,4-triazolidine-3,5-dione dissolved in sulpholane crystallises on cooling after completion of the reaction, which is easily recognised by the cessation of evolution of NH$_3$, and may be isolated by suction filtration or centrifuging.

Crystallisation may be accelerated if desired by the addition of inert solvents such as toluene, and the mother liquor obtained may be used again in the next batch while the toluene present is useful as a carrier agent for the water which is to be distilled off azeotropically, especially if the hydrazodicarbonamide is used directly as obtained in the moist state from the suction filter. The crystalline 1,2,4-triazolidine-3,5-dione obtained may normally be used directly for further processes, in many cases without even first being isolated.

An additional purifying effect is obtained by adding water to the hot sulpholane solution containing 1,2,4-triazolidine-3,5-dione, which causes triazolidine-3,5-dione to crystallise in a very pure form from the water/sulpholane mixture.

If cyclisation is carried out in solvents which are immiscible or only slightly miscible with water, such as the solvents of group B and, for example, diphenylether, then water is generally added dropwise with vigorous stirring at temperatures ≦150° C. to the cooling mixture after cyclisation, optionally using a condenser. Under these conditions, 1,2,4-triazolidine-3,5-dione dissolves in the aqueous phase. Sufficient water is added to form a 10 to 60% by weight aqueous solution of 1,2,4-triazolidine-3,5-dione. The hot aqueous solution is then separated from the organic phase and 1,2,4-triazolidine-3,5-dione. The hot aqueous solution is then separated from the organic phase and 1,2,4-triazolidine-3,5-dione is crystallised by cooling. 1,2,4-triazolidine-3,5-dione is obtained in a virtually pure state on drying and is immediately ready for use.

The solubility of 1,2,4-triazolidine-3,5-dione in water may, of course, be increased by the addition of an alkali liquor such as, for example, sodium hydroxide solution which leads to the formation of the corresponding sodium salt of 1,2,4-triazolidine-3,5-dione so that a small quantity of water is sufficient for removing 1,2,4-triazolidine-3,5-dione from the reaction vessel, with the result that the rate of throughput for each reaction batch is increased. The salt obtained in this way may be isolated and used for subsequent reactions or alternatively the salt may be reacted with an acid, e.g. hydrochloric acid, to release the pure 1,2,4-triazolidine-3,5-dione which then may be crystallised and isolated by filtration, suction filtration or centrifuging.

Water-immiscible organic solvents used in the process according to the invention are generally reused for subsequent reaction batches after removal of the aqueous 1,2,4-triazolidine-3,5-dione solution, and the aqueous mother liquors are also reused for separation and isolation of 1,2,4-triazolidine-3,5-dione.

1,2,4-Triazolidine-3,5-dione is a valuable starting material for the preparation of temperature-resistant units. Tris-hydroxyalkyl-triazolidine-3,5-dione, for example, which is one of the products obtained from this starting material, may be used as a cross-linking component in high-temperature-resistant electrically insulating lacquers and triglycidyl-triazolidine-3,5-dione prepared from 1,2,4-triazolidine-3,5-dione may be used, for example, as a cross-linking agent in powder lacquers used for the electrostatic powder spray process. 1,2,4-Triazolidine-3,5-dione is also used in photographic compositions.

The percentages given in the Examples are percentages by weight.

EXAMPLE 1

3 kg of sulpholane and 1.18 kg of air-dried hydrazdicarbonamide are heated to 200° C. within 2.5 hours in a 6-liter three necked flask equipped with stirrer, thermometer, dropping funnel and distillation bridge. A light vacuum is applied when ammonia begins to evolve at 150° to 160° C. The temperature is then raised to 210° C. within one hour. A clear solution is obtained after about 1.5 hours and this solution continues to be stirred at 210° C. and 200 mbar until the reaction is completed, i.e. for about 3.5 hours. The residual ammonia is removed at 40 to 80 mbar after cooling to 180° C. 0.8 kg of toluene are added dropwise to the cooling solution at normal pressure at such a rate that virtually no toluene distils off. The almost pure 1,2,4-triazolidine-3,5-dione which crystallises is suction-filtered after it has cooled to room temperature, and is then washed with toluene. 0.87 kg (86.2% of the theroetical yield) of dehydrated 1,2,4-triazoline-3,5-dione are obtained with a degree of purity of 97.5%, determined by titration with N/10 sodium hydroxide solution against phenolphthalein.

EXAMPLES 2–4

The mother liquor obtained in Example 1 is used for cyclising 1.18 kg of hydrazodicarbonamide as described in Example 1. The toulene dissolved in the mother liquor distils off when heated and may be reused for crystallisation. The yield is in all three batches from 94 to 97% of the theoretical yield and 1,2,4-triazolidine-3,5-dione is consistently obtained with the same degree of purity.

EXAMPLE 5

400 g of N-methyl-pyrrolidone and 160 g of hydrazodicarbonamide still moist from the suction filter (contains 73.8% of dry hydrazodicarbonamide) are heated to 205° C. in a one-liter stirrer apparatus similar to that of Example 1. The ammonia which begins to be released at 160° C. is expelled with nitrogen. After a reaction time of 3.5 hours at 205° C., about 300 g of solvent are distilled off in a water jet vacuum and acetone is added to the solution remaining behind. Triazolidine-3,5-dione which crystallises out is suction-filtered after it has cooled to room temperature and is then washed with acetone and dried. 74 g of a 97.5% pure 1,2,4-triazolidine-3,5-dione are obtained.

A further 16 g of a 96.5% 1,2,4-triazolidine-3,5-dione can be isolated from the mother liquor, so that the total yield is 90 g (89% of the theoretical yield).

EXAMPLE 6

Example 6 serves to demonstrate that the crude 1,2,4-triazolidine-3,5-dione obtained by the process according to the invention is sufficiently pure for further reaction without being isolated.

59 g of hydrazodicarbonamide in 100 g of sulpholane are cyclised as in Example 1 in a 500 ml four-necked flask equipped with stirrer, thermometer and reflux condenser. 1,2,4-Triazolidine-3,5-dione crystallises on cooling in such a highly concentrated form that a further 45 g of sulpholane are added to assist stirring. After the addition of 0.5 g of tetraethylammonium chloride, 66 g of ethylene oxide are introduced into the resulting suspension at 120° C. in the course of 6 hours through a subsequently installed gas inlet tube in such a manner that no ethylene oxide escapes. After completion of the reaction, the solvent is removed under a vacuum of 0.3 mbar. 120 g of crude N,N'N"-tris-(2-hydroxyethyl)-triazolidine-3,5-dione are obtained. According to gas chromatographic analysis, this dione contains 92% of pure triol and 2.8% of sulpholane. The crude bis-(2-hydroxyethyl)-triazolidine-3,5-dione, which begins to crystallise after several hours at room temperature, may be used either without further purification or after recrystallisation, e.g. from 3 parts of isopropanol and 7 parts of acetone for the preperation of, for example, high-temperature-resistant polymers such as polyesters or polyester imides, e.g. for the insulation of copper wire.

EXAMPLE 7

600 g of commercial m-cresol and 236 g of hydrazodicarbonamide are heated to 195° C. in 90 minutes under a stream of nitrogen in a 2-liter three-necked flask equipped with stirrer, thermometer and reflux condenser, and stirred for 5.5 hours at that temperature, and 200 ml of toluene are added dropwise as the solution cools. When the suspension has cooled to room temperature, it is suction-filtered, washed with toluene and dried. 160 g of a 97% 1,2,4-triazolidine-3,5 dione are obtained.

EXAMPLE 8

600 g of 1-methylnaphthalene and 300 g of moist hydrazodicarbonamide (contained 22.3% of water) are heated to 200° C. in a 2 liter four-necked flask equipped with stirrer, thermometer, dropping funnel and ditillation bridge and stirred at 200° C. under a light vacuum for 5 hours. 300 g of water are added dropwise while the reaction mixture cools, and the hot, aqueous phase is separated. Virtually pure 1,2,4-triazolidine-3,5-dione crystallises from this aqueous phase on cooling and may be isolated by suction filtration. 121 g of anhydrous 1,2,4-triazolidine-3,5-dione are obtained with a degree of purity of 96.7%, determined by titration with N/10 sodium hydroxide solution against phenolphthalein.

EXAMPLE 9

300 g of moist hydrazodicarbonamide (containing 22.3% of water) are cyclised in the organic phase from Example 8 as described in Example 8. 150 g of water and the aqueous mother liquor from Example 8 are added dropwise while the reaction mixture cools. After separation of the crystallised triazolidine-3,5-dione solution by suction filtration 163 g of dried 1,2,4-triazolidine-3,5-dione are obtained with a degree of purity of 95.2%.

EXAMPLE 10

1800 g of diphenylmethane and 1200 g of moist hydrazodicarbonamide (containing 22.3% of water) are heated to 205° C. in a 6-liter four necked flask which is equipped with stirrer, thermometer, dropping funnel and distillation bridge and to which is attached an outflow which can be opened with a tap. A light vacuum is applied when ammonia begins to evolve at 160° to 170° C. The reaction mixture is then stirred for 5 hours at 205° C. and the vacuum is raised to 200 mbar. While the solution cools down, 2.4 kg of water are added dropwise at normal pressure in such a manner that no water distils off. The hot aqueous solution is run off and left to cool with stirring. The almost pure 1,2,4-triazolidine-3,5-dione which crystallises out is suction-filtered and washed with 400 g of water. 528 g of dry 1,2,4-triazolidine-3,5-dione are obtained with a degree of purity of 97.9%.

EXAMPLES 11–13

The diphenylmethane obtained in Example 10 is used for cyclising 1200 g of moist hydrazodicarbonamide (containing 22.3% of water) as described in Example 10. The crude 1,2,4-triazolidine-3,5-dione obtained is isolated by dissolving it in 2600 g of an aqueous solution of mother liquor and wash water from Example 10 and then working it up as in Example 10. The yield in all three batches is from 730 to 760 g of 1,2,4-triazolidine-3,5-dione with a degree of purity ranging from 96.2% to 97.4%.

EXAMPLE 14

236 g of dried hydrazodicarbonamide and 600 g of diphenylether are heated to 205° C. in a 2-liter four-necked flask equipped with stirrer, thermometer, dropping funnel and reflux condenser. A light vacuum is applied when ammonia begins to evolve at 160° C. and is raised within 6 hours to 300 mbar. 400 g of water are added dropwise at normal pressure as the solution cools down, and the hot, aqueous solution is separated. The almost pure 1,2,4-triazolidine-3,5-dione which crystallises is suction-filtered after it has cooled to room temperature and is then washed with water. 132 g of dried 1,2,4-triazolidine-3,5-dione are obtained with a degree of purity of 98.3%.

EXAMPLE 15

236 g of dried hydrazodicarbonamide and 600 g of diphenylether are cyclised as in Example 14. The crude 1,2,4-triazolidine-3,5-dione is dissolved in the aqueous mother liquor from Example 14, separated and crystallised. After suction filtration, 193 g of dried 1,2,4-triazolidine-3,5-dione are obtained with a degree of purity of 94.2%.

We claim:

1. A process for the preparation of 1,2,4-triazolidine-3,5-dione, which comprises suspending hydrazodicarbonamide in at least one organic, water-miscible or water-immiscible solvent and cyclising it at a temperature in the range of from 150° to 280° C. and at a pressure of from 50 mbar to 5 bar with removal of the ammonia split off from the reaction mixture, and isolating the resulting 1,2,4-triazolidine-3,5-dione after crystallization.

2. A process according to claim 1, wherein cyclisation is carried out at a temperature of from 190° to 220° C. and at a reaction pressure of from 150 mbar to atmospheric pressure.

3. A process according to claim 1, wherein cyclisation is carried out in at least one organic polar solvent, and at least one other solvent, which is miscible with the cyclisation solvent, or water is added to the reaction mixture after cyclisation.

4. A process according to claim 1, wherein cyclisation is carried out in at least one organic solvent which is immiscible with water, and after cyclisation, while the reaction mixture is cooling down, at a temperature of from 60° C. to 150° C., water is added with stirring, optionally under reflux, in such a quantity that a from 10 to 60% aqueous solution of 1,2,4-triazolidine-3,5-dione is obtained, from which the 1,2,4-triazolidine-3,5-dione which crystallizes after cooling to room temperature is isolated.

5. A process according to claim 3, wherein the mother liquor obtained after removal of the 1,2,4-triazolidine-3,5-dione is re-used.

6. A process according to claim 4, wherein the organic solvent remaining after removal of the aqueous 1,2,4-triazolidine-3,5-dione solution is re-used.

7. A process according to claim 4 or 6, wherein the aqueous mother liquor obtained after the separation of crystalline 1,2,4-triazolidine-3,5-dione is re-used.

* * * * *